United States Patent
Giori et al.

(10) Patent No.: US 10,603,329 B2
(45) Date of Patent: *Mar. 31, 2020

(54) PHOSPHOLIPID COMPLEXES OF CURCUMIN HAVING IMPROVED BIOAVAILABILITY

(75) Inventors: Andrea Giori, Milan (IT); Federico Franceschi, Milan (IT)

(73) Assignee: INDENA S.P.A., Milan (IT)

( * ) Notice: Subject to any disclaimer, the term of this patent is extended or adjusted under 35 U.S.C. 154(b) by 2011 days.

This patent is subject to a terminal disclaimer.

(21) Appl. No.: 12/281,994

(22) PCT Filed: Feb. 21, 2007

(86) PCT No.: PCT/EP2007/001487
§ 371 (c)(1),
(2), (4) Date: Dec. 1, 2008

(87) PCT Pub. No.: WO2007/101551
PCT Pub. Date: Sep. 13, 2007

(65) Prior Publication Data
US 2009/0131373 A1   May 21, 2009

(30) Foreign Application Priority Data
Mar. 9, 2006  (EP) .................................... 06004820

(51) Int. Cl.
*A61K 36/9066* (2006.01)
*A61K 31/685* (2006.01)
*A61K 31/12* (2006.01)
*A61K 47/54* (2017.01)

(52) U.S. Cl.
CPC ............ *A61K 31/685* (2013.01); *A61K 31/12* (2013.01); *A61K 36/9066* (2013.01); *A61K 47/544* (2017.08); *A61K 2236/333* (2013.01)

(58) Field of Classification Search
CPC .... A61K 31/685; A61K 31/12; A61K 31/121; A61K 36/9066; A61K 47/544; A61K 2236/333
See application file for complete search history.

(56) References Cited

FOREIGN PATENT DOCUMENTS

CN          1657040 A       8/2005

OTHER PUBLICATIONS

Liu et al., "Validated LC/MS/MS Assay for Curcumin and Tetrahydrocurcumin in Rat Plasma and Application to Pharmacokinetic Study of Phospholipid Complex of Curcumin", J Pharm Biol Anal 40:720-27 (2006).
Began et al.. "Interaction of Curcumin with Phosphatidylcholine: A Spectrofluorometric Study", J Agri Food Chem 47:4992-97 (1999).

*Primary Examiner* — Theodore R. West
(74) *Attorney, Agent, or Firm* — Porzio Bromberg & Newman P.C.

(57) ABSTRACT

The present invention relates to novel phospholipids complexes of curcumin or extracts containing it having improved bioavailability.

5 Claims, No Drawings

PHOSPHOLIPID COMPLEXES OF CURCUMIN HAVING IMPROVED BIOAVAILABILITY

CROSS REFERENCE TO RELATED APPLICATION

This is a National Stage of International Application PCT/EP2007/001487, filed 21 Feb. 2007, which claims the benefit of Application No. 06004820.4, filed in Europe on 9 Mar. 2006, the disclosures of which Applications are incorporated by reference herein.

The present invention relates to novel phospholipids complexes of curcumin or extracts containing it having improved bioavailability.

TECHNOLOGICAL BACKGROUND

Curcumin, [1,7-bis(4-hydroxyl-3-methoxyphenyl)-1,6-heptadiene-3,5-dione], is the major constituent of the spice turmeric extracted from the root of *Curcuma longa* Linn. Curcumin is a polyphenol that has powerful antioxidant and inhibits the expression of the enzyme cyclooxygenase 2 (Cox 2) at least in part via interference with activation of the transcription factor NFkB [2, 14]. In vitro, curcumin inhibits the growth of cancer cells with an $IC_{50}$ value of 20-75 μM [6, 16]. In rodent models, curcumin has been shown to prevent cancer in the colon, skin, stomach, duodenum, soft palate, tongue, sebaceous glands and breast [9, 10, 15]. Therefore, curcumin could be considered a promising efficacious and safe cancer chemopreventive agents [18]. In fact, clinical pilot studies have associated curcumin consumption with regression of pre-malignant lesions of bladder, soft palate stomach, cervix and skin [1, 11].

However, concentrations of curcumin achieved in plasma and target tissues are low, probably due, at least in part, to its extensive metabolism by conjugation (glucuronidation and sulfation) and reduction pathways [4, 5, 7, 8].

Preclinical and clinical pilot studies suggest that In a phase I trial plasma and urine concentrations of curcumin in patients, who had ingested 3600 mg curcumin orally, were 11.1 nmol/L and 1.3 μmol/L, respectively [17]. In another study, peak plasma concentrations 1-2 h after oral dosing, reached 0.41-1.75 μM in patients receiving 4 to 8 g curcumin [1]. It is neither practical nor desirable to increase the oral dose of curcumin above that already investigated.

Therefore, it is highly desirable to find novel curcumin derivatives having improved bioavailability.

Complex compounds of vegetable extracts or of purified components thereof with natural, synthetic or semi-synthetic phospholipids, have been disclosed, e.g., in EP 209 038, EP 275 005, EP 283 713, EP 1 035 859 and EP 1 140 115. Said complexes improve the plasma bioavailability of the extract or purified component, thanks to their lipophilicity. EP 1 140 115 generically mentions ethanol among the various solvents that can be used of the preparation of said complexes, but does not provide preparation examples which make use of ethanol as the solvent. Furthermore, the complexes disclosed are phospholipid complexes of proanthocyanidin A2, which are quite different in the chemical structure with respect to the phospholipids complexes of curcumin of the present invention.

DISCLOSURE OF THE INVENTION

It has now been found that the phospholipids complexes of curcumin, providing higher systemic levels of parent agent than unformulated curcumin, can be prepared in protic solvents.

Therefore, the present invention relates to novel phospholipids complexes of curcumin having improved bioavailability.

According to the invention, phospholipids of either vegetable or synthetic origin can be used, particularly preferred are soy phospholipids, such as phosphatidyl choline, phosphatidyl serine, phosphatidyl ethanolamine.

According to the invention, the complexes are prepared by adding the phospholipid to curcumin dissolved in a protic solvent, more particularly adding the phospholipid to the ethanol solution of the hydroalcoholic extract of turmeric rhizomes, under reflux and with stirring. The resulting suspension is concentrated under reduced pressure to a residue which is dried in oven. The ratio of phospholipids to curcumin is in the range from 10 to 1 w/w, a more preferable mole ratio being 5:1 w/w.

The present invention also relates to pharmaceutical compositions containing as the active principle one of the phospholipids complexes of curcumin according to the invention, in admixture with a suitable pharmaceutical carrier.

The present invention further relates to the use of the phospholipids complexes of curcumin of the invention for the preparation of medicaments having chemopreventive action.

The following examples further illustrate the invention.

EXAMPLE 1

Preparation of Extract with a Low Content of Curcumin

Ground dry turmeric rhizomes (1000 g) were extracted with ethanol-water 9:1 mixture (6680 ml). The resulting hydroalcoholic solution was concentrated under reduced pressure and drying was completed in oven at 60° C. under vacuum to yield 69.3 g of an orange paste having a curcumin content of 17.4% w/w and a total curcuminoid content of 29.2% w/w.

EXAMPLE 2

Preparation of Extract with High Content of Curcumin

Ground dry turmeric rhizomes (1000 g) were defatted with hexane (2500 ml) before being extracted with ethanol-water 95:5 mixture (7500 ml). Curcuminoids were then crystallized by slowly adding hexane (500 ml) to the hydroalcoholic solution and allowing the resulting mixture to stand for 24 hours. A microcrystalline orange solid was filtered and dried at 60° C. under vacuum to yield 36.7 g of extract having a curcumin content of 71.74% and a total curcuminoid content of 93.8% w/w.

EXAMPLE 3

Preparation of the Complex from a Low-Content Extract 20 g of the product from Example 1 were dissolved in ethanol (400 ml) and the solution was refluxed. 30 g of soy phospholipids were slowly added in portions, under reflux and with stirring. The resulting suspension was refluxed with stirring for 1 hr, then hot concentrated under reduced pressure and finally dried in oven. 46.7 g of an orange waxy product were obtained, having a curcumin content of 7.54% and a total curcuminoid content of 12.1% w/w.

While the starting extract is insoluble in chlorinated solvent, the resulting product is soluble in $CHCl_3$ in a 4% w/v concentration thus confirming the complexation of the extract by the phospholipid and the formation of a molecular complex.

The $^1$H-NMR spectrum of the complex in $CDCl_3$ shows the main signals of the phospholipids, typical of complexed phospholipids. On the other hand, the $^1$H-NMR spectrum of the complex in DMSO-$d_6$, which is a solvent preventing the aggregation of the complex, shows the signals of the free starting extract as well as those of the phospholipids.

In the $^{31}$P-NMR spectra, the signal of $^{31}$P in $CDCl_3$ is at 1.06 ppm and is 35.3 Hz wide, which is typical of complexed phospholipids. The complex is destroyed in DMSO-$d_6$ as confirmed by the signal of $^{31}$P at 0.12 ppm with 3.80 Hz width typical of the free phospholipid.

EXAMPLE 4

Preparation of the Complex from a High-Content Extract 20 g of turmeric rhizomes extract having a total curcuminoid content of 93.8% w/w were dissolved in ethanol (800 ml) and the solution was refluxed. 80 g of soy phospholipids were slowly added in portions, under reflux and with stirring. The resulting suspension was refluxed with stirring for 1 hr, then hot concentrated under reduced pressure and finally dried in oven. 97.6 g of an orange waxy product were obtained, having a curcumin content of 13.2% and a total curcuminoid content of 16.9% w/w.

The solubility of the product in $CHCl_3$ at a concentration of 4% w/v and the NMR spectra are the same as those of Example 3, confirming the formation of the complex.

EXPERIMENTAL SECTION

Tests were carried out to compare curcumin bioavailability afforded by the phospholipid complexes of the invention and by the extract containing uncomplexed curcumin.

Materials and Methods

Male Wistar rats (250 g) were fasted overnight and received by oral gavage either extract obtained by Example 2 or complex obtained by the Example 4 at dose of 340 mg/Kg in terms of curcumin.

Rats were killed at 15, 30, 60 and 120 min. Whole blood was collected into heparinized tubes, centrifuged immediately at 7000×g for 15 min, plasma was then decanted and stored at −80° C. until analysis.

The presence of curcumin and metabolites was verified by negative ion electrospray liquid chromatography/tandem mass spectrometry as previously described (4, 5, 7).

Pharmacokinetic Analysis

Peak plasma levels and area under the plasma concentration time curve (AUC) values for parent curcumin after administration of curcumin complexed with phospholipids as described in Example 4 were five-fold higher than the equivalent values seen after treatment with extract of Example 2 (uncomplexed curcumin) (Table 1).

TABLE 1

Estimated plasma Cmax, Tmax and AUC values for unformulated and formulated curcumin.

|  | Cmax (nM) | $T_{max}$ (min) | AUC (μg · min/mL)* |
|---|---|---|---|
| Extract of Example 2 |  |  |  |
| Curcumin | 6.5 ± 4.5 | 30 | 4.8 |
| Curcumin glucuronide | 225 ± 0.6 | 30 | 200.7 |
| Curcumin sulfate | 7.0 ± 11.5 | 60 | 15.5 |
| Complex of Example 4 |  |  |  |
| Curcumin | 33.4 ± 7.1 | 15 | 26.7 |
| Curcumin glucuronide | 4420 ± 292 | 30 | 4764.7 |
| Curcumin sulfate | 21.2 ± 3.9 | 60 | 24.8 |

*AUC was calculated using WinNonLin and employing a non-compartmental model.

Results

The results show that the phospholipids complexes of curcumin of the invention provides higher systemic levels of parent agent than uncomplexed curcumin.

The improved bioavailability of phospholipid complex of curcumin increases the potential scope of medical applications for curcumin as a chemopreventive agent.

REFERENCES

1. Cheng A L, et al., Anticancer Res 21: 2895-2900.
2. Duvoix A, et al., Cancer Lett 223: 181-190.
3. Fagerholm U, et al., J Pharm Pharmacol 50: 467-443.
4. Garcea G, et al., Br J Cancer 90: 1011-1015.
5. Garcea G, et al., Cancer Epidemiol Biomarkers Prev 14: 120-125.
6. Goel A, et al., Cancer Letters 172: 111-118.
7. Ireson C, et al., Cancer Res 61: 1058-1064.
8. Ireson C, et al., Cancer Epidemiol. Biomarkers & Prev 11: 97-104.
9. Kawamori T, et al., Cancer Res 59: 597-601.
10. Kelloff G J, et al., J Cell Biochem 63: 54-71.
11. Kuttan R, et al., Tumors 3: 29-31.
12. Li, L., et al., Cancer 104: 1322-1331.
13. Mourao S C, et al., Int J Pharmaceut 295: 157-162.
14. Plummer S M, et al., Oncogene 18: 6013-6020.
15. Rao C V, et al., Cancer Res 55: 259-266.
16. Shao Z-M, et al., Int J Cancer 98: 234-240.
17. Sharma R A, et al., Clin Cancer Res 10: 6847-6854.
18. Surh Y J Nature Rev Cancer 3: 768-780.
19. Workman P, et al., Brit J Cancer 77: 1-10.

The invention claimed is:

1. A phospholipid complex of curcumin or an extract containing it, obtained by a process comprising the steps of:
   reacting a hydroalcoholic extract of turmeric rhizomes with a phospholipid in ethanol and isolating the complex by concentration and drying.

2. The complex of claim 1, wherein the phospholipid is a soy phospholipid.

3. The complex of claim 2, wherein the phospholipid is selected from phosphatidyl choline, phosphatidyl serine, phosphatidyl ethanolamine.

4. A pharmaceutical composition containing as the active principle the complex as claimed in claim 1 in admixture with a suitable pharmaceutical carrier.

5. A pharmaceutical composition containing as the active principle the complex as claimed in claim 2 in admixture with a suitable pharmaceutical carrier.

* * * * *